US005976579A

United States Patent [19]
McLean

[11] Patent Number: 5,976,579
[45] Date of Patent: Nov. 2, 1999

[54] NUTRITIONAL SUPPLEMENT FOR THE PREVENTION AND TREATMENT OF EXCESSIVE INTESTINAL PERMEABILITY

[76] Inventor: Linsey McLean, 4267 S. State Rd., Davison, Mich. 48423

[21] Appl. No.: 08/887,909

[22] Filed: Jul. 3, 1997

[51] Int. Cl.$^6$ .......................... A61K 33/08; A61K 33/00; A61K 31/315; A61K 31/195
[52] U.S. Cl. .......................... 424/692; 424/715; 514/494; 514/561
[58] Field of Search .................................... 424/692, 715; 514/494, 561

[56] References Cited

U.S. PATENT DOCUMENTS

| | | | |
|---|---|---|---|
| 4,582,709 | 4/1986 | Peters et al. | 426/74 |
| 4,774,089 | 9/1988 | Ashmead | 424/157 |
| 5,215,750 | 6/1993 | Keane, II | 424/440 |
| 5,496,567 | 3/1996 | McLean | 424/692 |

OTHER PUBLICATIONS

David Granstrom, "Equine Protozoal Myeloencephalitis", *The Horse*, Sep. 1995, pp. 5–9.
Malcolm S. Gordon, "Animal Physiology: Principles and Adaptations", 2nd Edition, 1972, p. 520.
Philip H. Mitchell, "A Textbook of General Physiology", Fifth Edition, 1956, pp. 441, 472–477, 576–580, 678–681.
Marjorie Hurt Jones, "Leaky Gut –What Is It? What Factors Cause It? What Can Be Done? An interview with Leo Galland, M.D.", *Mastering Food Allergies,* Jul.–Aug. 1995, vol. X, No. 4, pp. 1–8.
Laura Hillenbrand, "Beating EPM", *Equus 219,* pp. 30–36.
Dr. John Madigan, "Equine Protozoal Myelitis Workshop", *Equine Veterinary Data,* vol. 16, No. 1, 1995, pp. 46 and 47.
Kathleen Yvorchuk, "Protozoal Myeloencephalitis", *Protozoal Myeloencephalitis,* pp. 554 and 555.
Dr. Robert J. MacKay, "Equine Protozoal Myeloencephalitis", *The Compendium,* vol. 14, No. 10, Oct. 1992, Continuing Education Article #6. pp. 1359–1366.
Laurie Flo, University of California at Davis Equine Research Laboratory, "More About Equine Protozoal Myelitis (EPM)", pp. 32 and 34.
"Healthscene", *Health Counselor,* vol. 6, No. 6, p. 12.
Richard P. Huemer, M.D., "Preventive Medicine", *Let's Live,* Mar. 1995, p.82.

*Primary Examiner*—Raymond Henley, III
*Attorney, Agent, or Firm*—Harness, Dickey & Pierce, P.L.C.

[57] ABSTRACT

A nutritional supplement for the prevention and treatment of excessive intestinal permeability is provided. The treatment includes a dietary regimen of nutritional buffers, amino acid chelates, minerals and vitamins. Other components may include antioxidants, free radical scavengers, beneficial organisms, and intestinal tract-soothing herbs.

14 Claims, No Drawings

NUTRITIONAL SUPPLEMENT FOR THE PREVENTION AND TREATMENT OF EXCESSIVE INTESTINAL PERMEABILITY

BACKGROUND OF THE INVENTION

I. Field of the Invention

The present invention relates to a nutritional supplement for treating and preventing excessive intestinal permeability in living systems. The composition of the present invention provides nutritional buffers to the gastrointestinal tract as well as buffered, optimal amounts of amino acid chelates, minerals, and vitamins. Furthermore, the composition optionally may include antioxidants, free radical scavengers, beneficial organisms to restore intestinal health, and tract-soothing herbs.

II. Description of the Relevant Art

In the past thirty years, there have been many environmental changes affecting agriculture and the foods eaten by both animals and humans. The most notorious three factors affecting nutritional status of our foods and feeds are toxic environmental chemicals, acid rain, and the commonly unrecognized impact of the new super phosphate fertilizers having the composition 0-0-46.

Toxic environmental chemicals fall into two general categories. The first category comprises organic compounds including pesticides, herbicides, solvents and other industrial chemicals. These organic compounds are known to affect hormone status in biological systems, mimicking both androgens and estrogens. Healthy biochemistry includes the suppression of, activation of, and competition with natural hormones in the biological system, whether the system is plant, animal or bacterial in nature.

The second category of toxic environmental chemicals comprise heavy metal and halogen compounds. Heavy metals are known to substitute themselves for nutritional metals or minerals in enzyme systems and other biochemical pathways that are dependent upon nutritional metals or minerals. This especially occurs under conditions of excessive exposure to the heavy metals combined with nutrient metal or mineral deficiency.

Halogen compounds (containing fluorine, chlorine, bromine, and/or iodine) are often organic as well, multiplying their potential for toxicity. The law of halogen replacement, which describes the chemical personalities of the halogens, states that the electro-negativity of the halogens decreases progressively with increase in atomic number. Each halogen tends to displace those below it in the Periodic Table. Fluorine is the most electronegative of all of the halogen elements, followed by chlorine, bromine and finally iodine. Iodine is necessary for the thyroid hormone thyroxine which plugs into special receptor sites on the cell membranes of every cell in an animal system, regulating the speed of biochemical reactions at the cellular level. Thus, thyroxine is the master regulator of basal metabolism. The molecule thyroxine is composed of two molecules of the amino acid tyrosine bonded to four molecules of iodine, commonly called T4. The T4 molecule, known as the storage form of the thyroid hormone, is then enzymatically deiodinated to T3 (whereupon it contains only three iodine molecules) to free a bonding site for the receptor on the cell membrane. This now becomes the active form of the thyroid hormone in the animal body.

Because the law of halogen replacement, iodine, which is essential in animal and human biochemistry, brings up the rear in halogen chemical activity. Iodine is the least active of this family and can be easily displaced and substituted for by any of the other halogens. With reference to the thyroxine molecule, many intermediary biochemical pathways can be shut down in thyroid metabolism, as enzymes, cofactors and feedback mechanisms become confused by the deception if such a substitution occurs. Medical testing and diagnosis of thyroid function and dysfunction are also confused by the similarity of electron clouds, and differences in size and molecular weight of the displaced substituted lighter halogens for iodine. False negatives and positives in medical testing are possible, as well as skewed autoantibody titres, from autoimmune responses directed at the improper molecule trying to mimic the natural one. The measurement of levels of T3 and T4, which is the typical thyroid profile used as a screening tool for hypothyroidism in every medical office, can also be affected. Statistically, a full 60–65% of testees falling into the so-called "normal" category are symptomatic for clinical hypothyroidism and/or myxedema associated with hypothyroidism. The potential for biochemical disaster involving this displacement substitution, coupled with the higher toxicity of the other halogens themselves, sets the stage for the epidemic syndromes seen today which are variously depicted as chronic fatigue syndrome, clinical depression, morbid obesity, attention deficit disorder (ADD), attention deficit hyperactivity disorder (ADHD), and addiction syndromes resulting from clinical depression. These syndromes are frequently characterized by many faulty blood sugar regulation and hormone imbalances which are conditions involving lowered basal metabolism and metabolic rates. These statistical observations are exemplified in universally lower basal temperatures, particularly noted in the human population. Hardly anyone regularly records a basal temperature of 98.6° F. anymore. New "normals", reflecting these statistical observations are not associated with optimum health, and are more in the 96–97° range. This halogen causative factor in particular is highlighted in this invention, because thyroxine function in the body is known to regulate the absorption and metabolism of calcium and magnesium, the biological system's major cation buffers.

Acid rain affects the pH of the soil and subsequently the plants grown on it, showing a drop toward more acidic levels. Acid rain is known to affect both macro and micro mineral status as bioavailability for plants in a negative way, by binding and making these essential elements unavailable for use. Plants have not responded to the new soil nutritional deficiencies because they are simple organisms, much less complicated than the animal organisms who rely on them for food. Plant essential nutrients are limited to nitrogen, phosphorus, and potassium, while the animals (including man) who depend on them for food require many additional elements such as copper, zinc, manganese, cobalt, selenium, vanadium, etc. Plants simply take these additional elements up only incidentally. These additional elements do not significantly increase crop yield, for, as previously mentioned, they are not absolutely essential to plant growth. Upon recognition of these deficiencies coming through our foods and feeds by the more nutritionally aware organic farming movement, a great effort was launched some 20 years ago to improve the elemental nutritional status of soils, and hopefully the resulting foods and feeds produced. This great effort proved to be a failure, in that the fertilization practices involving the additional trace minerals previously mentioned did not significantly increase crop yield, and, subsequently, did not offer a payback to the organic farmers who spent great quantities of money in this experiment. In light of this information it now becomes more important to supplement these vanishing elements in the food of the animals and man who depend upon these now increasingly more deficient foods for sustenance and health.

Super phosphate fertilizer, a relatively new invention of the fertilizer industry, was created in response to the oil embargo of the early 1970s which so crippled the American economy. Traditionally, farmers used 30–40 lbs. per acre of conventional phosphate fertilizer for optimum grain production. In answer to the great demands of agriculture during this embargo for oil-based phosphate fertilizers, much research was done to try to reduce our requirements for oil in this industry thus to reduce the kind of dependence on foreign oil we had developed. The fertilizer industry was one of the largest users of oil resources. With super phosphate fertilizer, the 30–40 lb. requirement per acre of traditional phosphate fertilizer can be reduced to 2 lbs. per acre, which is a highly significant savings. The reduction can be accomplished because of the increased biological activity of the new phosphate chemical forms over the old phosphates. This higher phosphorus activity places a greater pressure against calcium and magnesium activity, the phosphorus element's antagonists and natural balancing elements. Calcium and magnesium are also the living organisms' major buffering elements, involved both at the cellular level as well as in the digestive tract. Greater phosphate activity, relative to calcium and magnesium activity, translates to the farmer as accelerated maturation of the grain plant, earlier harvest times, and less plant residue on fields after harvest due to stunted plant green growth dependent on calcium and magnesium. These super phosphate residues are now coming through food and feed sources for our food animals and ourselves. It is no coincidence that human population statistics are now showing earlier menarche and earlier menopause in girls and women. Population statistics also confirm higher calcium and magnesium deficiency syndromes, such as osteoporosis, at an ever earlier age as well.

This reduction of calcium and magnesium bioavailability and biological activity as a result of the combined negative environmental and technological influences causes depressions in buffering activity at the cell level in the animal system, allowing the accumulation of higher levels of acidic byproducts of cell metabolism, such as lactic acid. In the digestive tract, this downward pH shift contributes to the formation of ulcers and malabsorption syndrome, from incompletely buffered and therefore unabsorbable nutritional digestive components. The downward pH shift in the digestive tract also shifts the microbiological environment toward a favorability of acid accommodating, acidophilic and fermentative organisms, instead of those most suitable to aid digestion. The desirable symbiotic organisms are responsible for the production of B-complex vitamins, certain essential amino acids, and other intermediary metabolites that aid the host body. The host body has evolved to rely on this source of essential nutrition. Loss of this essential source of nutrition presents significant nutritional deficiencies affecting the inherent quality of life.

The combined effect of the downward pH shift in the digestive tract, associated with various environmental changes described above, is the factor acting as the major contributor to excessive intestinal permeability described as "leaky gut syndrome", with the corresponding associated allergy, parasitic and immune depression syndromes well documented in human medicine.

Excessive intestinal permeability (or "leaky gut syndrome") is the inability of the biological system to properly buffer the chyme ingredients of the small intestine. The lowered pH then irritates the membranes of the digestive system causing fragility and breakage of cell membranes at the cellular level, and leakage of digestive contents outside the digestive tract. Cell membranes are only two molecules in thickness, composed of a high percentage of protein, whose peptide bonds linking the amino acids, are highly susceptible to subtle downward pH shifts. These lowered pHs cause proteins to deform and change shape. This deformation can be demonstrated by adding milk to orange juice and watching the curds of deformed milk proteins form, in response to the lowered pH of the mixture containing citric acid. If the curdled milk/orange juice mixture is then buffered with baking soda, or the like, raising the pH, the curdles disappear and the mixture creams, as the milk proteins regain their shape again. When the proteins of the cell membranes become deformed from overexposure to this lowered pH shift action, the micropores in the cell membranes, which allow for influx of nutrients and outward flow of cellular waste products, become deformed as well, and essentially close off. This triggers inflammatory response and cell death by starvation and waste intoxication.

The integrity of the cell membrane is also essential for the electrical and energy mechanisms of the cell, with the cation electrolytes, magnesium and potassium inside the cell, balancing the cation electrolytes, calcium and sodium in the fluid outside of the cell. This function is similar to a car battery with its two chemical cells divided by a metal plate. Electrical activity across this plate is the source of electrical/chemical energy in the battery. The cell membrane is akin to this medial plate, across which electrical/chemical activity between the cations takes place. This is a major source of energy for the cell. Destruction of the cell membrane, all or in part, allows calcium and sodium to rush into the interior of the cell, essentially shutting down this electrical/chemical activity. The same thing happens to a car battery when the plate between the two cells is removed and chemicals from both cells are allowed to combine. When the cell membrane is destroyed, the cell itself is effectively destroyed. If this happens to take place along the intestinal walls of the gastro-intestinal tract, commonly the first area of the body affected by excess environmental acidity, fracturing of the tissues of the intestinal walls occurs. This then opens the door, so to speak, for invasion of inner tissues and cavities of the body by digestive contents. Here is where the allergic reactions and migrations of opportunistic microbiological and/or parasitic organisms are born, overwhelming the immune system to virtual exhaustion. Combined with the previously-described induced nutritional deficiencies, immune depression commonly results. Carrier proteins of trace minerals from the digestive tract are also affected, contributing to nutritional mineral deficiencies.

Since virtually any protein can be affected anywhere in the body by these lowered pH changes, the biochemical activity of enzymes, hormones, biochemical receptor sites, feedback mechanisms, and neurotransmitters are also affected, since these are proteins. This complicates physical conditioning and performance, as well as promoting behavioral changes, including clinical depression, anxiety, learning disabilities, and hyperactivity syndrome, among others. In fact, the combined effects of all of these aforementioned causative factors are the root of the commonly diagnosed gigantic category of "environmental illness".

SUMMARY OF THE PRESENT INVENTION

The present invention provides a solution to the problems described above by offering a nutritional supplement for treating and preventing excessive intestinal permeability in living systems. The composition of the present invention provides nutritional buffers to the gastrointestinal tract as well as buffered, optimal amounts of amino acid chelates, minerals, and vitamins. Furthermore, the composition optionally provides antioxidants, free radical scavengers, beneficial organisms to restore intestinal health, and tract-soothing herbs.

DETAILED DESCRIPTION OF THE PREFERRED EMBODIMENTS OF THE PRESENT INVENTION

The present invention mitigates the adverse biochemical and behavioral responses to the described environmental causative factors, in these general ways:

1. To supply nutritional buffers to the gastrointestinal tract, to aid the animal body restoring the proper buffering of chyme, which in turn promotes proper absorption of nutrients, and protection from excess acid destruction of cell membranes in the digestive tract, thereby preventing excessive intestinal permeability. These nutritional buffers also aid in the promotion of health and in the healing of existing gut fractures.

The maintenance of proper intestinal pH is also important in maintaining resistance to opportunistic migrations of microbiological and/or parasitic organisms. These pathogens and potential pathogens are normally ingested in encapsulated cyst form, and must be exposed to a lengthy time in acid media to break the encapsulation and become free living as a trophozoite form. This active, free living form is capable of completing its life cycle and reproduction. Cystic encapsulation in the inactive stages of the life cycles of these microbiological and/or parasitic organisms provides protection from environments not conducive to the completion of their life cycles. This adaptation assures protection from extinction and continuation of the species, since these organisms have no control over the environments in which they find themselves.

A perfect and representative example is seen today as the epidemic of a disease not previously observed in the horse population of the United States to any degree. Called "Equine Protozoal Myelitis", this disease is descriptive of protozoal trophozoites or free living forms, migrating through the tissues of the body, including the central nervous system, and causing various and sundry lamenesses, ataxias and behavioral changes. At this time no single causative agent has been identified, but many different protozoa have been implicated. What makes this example so relevant is the fact that the horse, a grazing vegetarian, has become susceptible to such a huge degree as to cause up to 80% of the horse population of a given area to test positive for blood antibodies to the most commonly implicated, and the most notoriously invasive, of the protozoa species, Sarcocystis neurona. This pathogenic protozoa has previously only been found in carnivores, such as opossums and raccoons. It is known that carnivores have a lower gut pH than vegetarians, and particularly vegetarian grazing animals such as horses. The environmental changes that have been described here explain why the previously unthinkable is now commonly observed whereby that grazing vegetarians (in this example, horses) would now become susceptible, en masse, to the same diseases and parasitic infections that plague a carnivore. Statistics from university research over ten years ago describe the incidence of ulcers in horses occurring in between 52 and 90% of the entire horse population, relating to different breeds, ages and work loads. Biologically, this should not be possible unless the living environment of all of these horses has changed dramatically in the same ways and for every horse to significantly lower the pH of the digestive tracts of these grazing vegetarians. Ulcers in grazing vegetarians should not even be possible under normal conditions, indicating that the abnormal exists.

Microbiological and/or parasitic organisms have evolved a mechanism by which they can monitor their environments and respond only when conditions are favorable for completion of their life cycles. This adaptive advantage is the development of a thick wall around a "hibernating", inactive stage of life. Only after lengthy exposure to a low pH liquid environment, which in effect "digests" or destroys this thick wall and triggers activation of the organism, does the organism emerge as a free form or trophozoite, able to complete its life cycle and reproduce. One can see how a protective mechanism, such as this thick wall, can prevent extinction for the species and promote proliferation. If the encapsulated cyst happens to land in a mud puddle caused by rain, only to dry up within a short time, the conditions would not have been met to satisfy the requirements for life cycle completion. If the encapsulated cyst were to fall, on the other hand, in the waters of a swamp, the pH of the water, sufficiently low from the rotting vegetation in the water, would trigger the destruction of the thick wall and activate the organism to complete its life cycle. In this way the organism would, by the pH of the water, "know" when conditions were right which is in turn dictated by the length of time the water had been standing. Longer standing water is generally lower in pH, and the chances are that the longer the water has been standing, the longer it will continue to stand to provide adequate time for completion of one or many life cycles. Exposure to excessive acids in a digestive tract, not able to be buffered properly within a suitable time frame, mimics this natural chain of events in the wild for these microorganisms. Hence, their opportunistic, pathogenic nature and their epidemic disease occurrences in previously non-target hosts.

The active trophozoite form, or free living forms of these organisms, released from their protective encapsulation by excess gastrointestinal acids, are now capable of migration through tissues, even to cerebrospinal fluid, causing ataxias and other various and sundry physical dysfunctions, depending upon the location of migration and the corresponding inflammatory reactions they elicit. Species not commonly regarded as "pathogenic" or having the innate ability to invade the body on their own, can, with the door to the interior tissues and body cavities opened through membrane fractures or increased intestinal permeability, now become opportunistic pathogens. This situation is likened to an open door to a candy shop, with candy sitting out in full view of a 5-year old child passing by. Normally, this young child would not think of going into a candy store through a closed door to help himself to the candy. But, the situation changes as opportunities and temptations arise with the open door. A young, innocent child becomes, under the right conditions, a thief. So too with common intestinal inhabitants previously regarded as innocent or "non-pathogenic and normal" fauna and flora.

In the current epidemic of equine Protozoal Myelitis, previously thought harmless, species of intestinal protozoa show up in increasing numbers as trophozoites or free living forms, in fresh fecal smears and hemolyzed blood, corresponding to the severity and numbers of physical dysfunctions.

2. To supply in a buffered, bioavailable form, optimal amounts of macro and micro nutrient metals, minerals, and vitamins necessary to promote optimum health, to overcome soil and food mineral and nutritional deficiencies, to fuel biochemical pathways and enzyme systems in the living animal system, and to restore proper immune function, so necessary to destroy invaders of tissues and body cavities that have already entered through the intestinal walls, via increased intestinal permeability or "leaky gut syndrome".

3. To provide ample amounts of antioxidants and free radical scavengers, which reduce inflammation and inflammatory responses, themselves contributing to physical and/or behavioral dysfunctions.

4. To supply "probiotic" cultures of beneficial organisms to replenish intestinal microbes necessary for good intestinal health.

5. To soothe the inflamed gastrointestinal tract and provide immediate comfort to the affected body with soothing herbs such as peppermint.

Preferred components of the composition of the present invention include the following.

Calcium carbonate, an antacid, in the approximate amount of 58.9421% by weight.

Sodium sesquicarbonate, used in bath crystals and as a food additive, in the approximate amount of 26.9552% by weight. Note that potassium bicarbonate or sodium bicarbonate or any other carbonate source could be substituted for sodium sesquicarbonate, if proper calculations for carbonate equivalent ions were done. Sodium bicarbonate is not as free flowing for manufacturing purposes and contains, on the whole, more sodium per carbonate or buffering per kilogram. This is less desirable in humans, but satisfactory for other vegetarian species like horses, who tend to retain potassium and require more sodium.

Magnesium oxide, used in pharmaceuticals and cosmetics, in the approximate amount of 4.7441% by weight.

Dimethyl glycine HCL in the approximate amount of 1.0415% by weight.

Vitamin E (50%) (tocopherol), essential in nutrition and used in medicines, as an antioxidant for fats, and as an animal feed additive, in the approximate amount of 3.5941% by weight. Note that various percentages of vitamin E can be used as equivalents, with proper calculations to convert, a 50% vitamin E supplement is most available to us at this time.

A vitamin B-complex blend, essential for the maintenance of neurologic and cellular function, in the approximate amount of 2.3002% by weight.

Potassium amino acid complex in the approximate amount of 0.2717% by weight.

Selenium amino acid chelate in the approximate amount of 0.3993% by weight.

Copper amino acid chelate in the approximate amount of 0.0831% by weight.

Zinc amino acid chelate in the approximate amount of 0.2038% by weight.

Manganese amino acid chelate in the approximate amount of 1.5623% by weight.

Iodine amino acid chelate in the approximate amount of 0.0687% by weight.

Chromium amino acid chelate in the approximate amount of 0.0000638% by weight.

Note that other bioavailable chemical forms of minerals may be substituted for the mineral chelates if the equivalent numbers of elemental minerals are met.

Pyridoxine hydrochloride, used for basic nutrition and for medicines, in the approximate amount of 0.0415% by weight.

Vitamin A in the approximate amount of 0.0958% by weight.

Vitamin D in the approximate amount of 0.0958% by weight.

In addition, a flavoring compound is provided in an amount sufficient to enhance palatability in animal mixtures.

Daily dosage is calculated by weight and species. Monogastric animals will need more per pound of body weight than ruminants, because of the beneficial help the rumen bacteria give the animals. Typical dose for horses would be 75–150 grams per day of the formula, depending on age, breed, sex and workload or stress level and symptomology.

Average daily dose for an adult person would be 15–30 grams per day, depending on stress level and symptomology. Animals and humans showing signs of autoimmune or chemical hypothyroidism or hypoadrenalism would require the high end amounts.

EXAMPLE

A typical batch of the formula consists of:

| | |
|---|---|
| Calcium Carbonate | 18.45 kg |
| Sodium Sesquicarbonate | 8.437 kg |
| Magnesium Oxide | 14.85 kg |
| Dimethyl Glycine HCL | 326.025 g |
| Vitamin E - 50% | 1.125 kg |
| B-complex blend | 0.72 kg |
| Selenium Amino Acid Chelate | 125 g |
| Potassium Amino Acid Complex | 85.05 g |
| Copper Amino Acid Chelate | 26 g |
| Zinc Amino Acid Chelate | 63.7875 g |
| Manganese Amino Acid Chelate | 489.0375 g |
| Pyridoxine Hydrochloride | 13 g |
| Iodine Amino Acid Chelate | 21.5 g |
| Chromium Amino Acid Chelate | .02 g |
| Vitamin A | 30 g |
| Vitamin D | 30 g |

A flavoring compound—enough to enhance palatability in animal mixtures.

Clinical Trials

Clinical trials were done on performance horses of the highest caliber, either racing horses or high level show horses, where trainers were sensitive enough to observe subtle changes in attitude, behavior and physical performance. Horses were chosen for clinical trials because of the high level of focus on the epidemic proportions of Equine Protozoal Myelitis, the development of two new diagnostic tests used in both blood and cerebrospinal fluid (CSF) testing for antibodies to Sarcocystis and DNA for the presence of the actual organism. These tests monitor the presence of the actual organism and its extent of migration through the body as well as the ability of the immune system to respond to it. There is as yet no such testing for humans, except for C-reactive protein which is not specific for general inflammatory responses. Horses also do not exhibit the placebo effect as they do not know what they are being fed or for what purpose. Furthermore, their performances are measurable in 15th of a second increments. Their food sources are the same everyday, as well as are their living conditions. They are not subject to such human traumas as emotions, excessive living, relationship-induced depression, addictions to nicotine, alcohol or recreational drugs (all monitored by the racing commission and Federation Equestre Internationals [FEI]). This makes them the ideal candidates for clinical trials as they are conditioned athletes, receiving the highest level of care, with essentially no other outside factors to influence the data.

Clinical trials were conducted using the following protocol:

Videotaped complete neurological examination by a licensed veterinarian whose practice is limited to, and specializes in, performance horses Feeding of the formula three times per day Repeated videotaping by the same veterinarian of complete neurological exam every two weeks to monitor progress Evaluation of progress Two categories of horses were studied, both having been positively diagnosed by blood and CSF for EPM.

A. Horses successfully treated by the common prescription drug combination currently in use, but relapsed when taken off the drugs anywhere from five days to two months, all other factors remaining the same B. Horses never having been treated with the prescription drugs but receiving the formula of the present invention instead. All other factors remained the same.

Results: Positive responses were noted in both categories of horses about the third day. Between the fifth day and the tenth day, a worsening of symptoms and/or a rise in temperature to low grade fever was often noted, indicating the beginning of a healing crisis initiated by the restoration of the immune system and a greater response to foreign organisms already in occupation of the interior tissues of the body. This healing crisis lasted from one to seven days, after which significant progress was noted which continued until full recovery and alleviation of the symptoms between two and eight weeks depending on the severity of symptoms and the length of duration of disease.

Compared to conventional drug therapy, horses administered the formula of the present invention suffered no ill effects, depression of the immune system identified by lowered white cell count, muscle wasting, or depression so commonly reported with conventional drug treatment, and their end level of health attained was higher and with more successful performance results than with conventional drug therapy. The monitoring of hemolyzed blood samples for free living protozoal forms, migrated from the intestine, showed the presence of living trophozoites in untreated and relapsed horses, but not in horses fed the invention beginning between three and five days after commencement of treatment to the conclusion of the trial two to four months later. This shows the effectiveness of the invention in preventing migration of free living or trophozoite forms to the interior tissues of the body as exemplified by their presence in blood. As a result of the success of these trials, most all of the trainers elected to keep their horses on the invention indefinitely. Microbiological inspection of the fresh feces in horses under current prescription drug therapy, past drug therapy with relapse (category A), and untreated horses of Category B, all showed excessive trophozoite numbers, capable of migration, relative to encapsulated, harmless, cystic forms. Within three days of administering the invention, the relative number of trophozoite or free living forms to the encapsulated, harmless forms, was greatly reduced, in some horses approaching zero, showing the effectiveness of the invention, preventing activation of at least three observed species of protozoa.

Horses utilizing the invention also showed less susceptibility to secondary infections, with which some were constantly plagued, and greater resistance upon exposure to contagious diseases exhibited by other horses in the same barn, showing the effectiveness of the invention and restoring the capabilities of the immune system.

Horses that had been hindered biochemically in their training and performance and only marginally helped by up to six months use of conventional drug therapy were able to go to subsequently higher levels of training and performance after only three weeks use of the invention, showing the effectiveness of the invention in fueling and refueling normal biochemical pathways toward the restoration of health.

In comparison with conventional drug therapy, horses being fed conventional drugs for between six months and up to two years still showed the same high numbers of free living or trophozoite forms of protozoa as untreated animals in fresh fecal smears, and had free living forms present in hemolyzed and fresh blood as well. In fact, the longer the duration of drug therapy, the higher the numbers of protozoa observed in the blood, indicating the probability of development of resistance to the drugs.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A dietary supplement for the prevention and treatment of excessive intestinal permeability, the supplement including a carbonate in the amount of at least 50% by weight, at least one amino acid chelate, at least one mineral, and at least one vitamin.

2. The dietary supplement of claim 1, wherein said at least one amino acid chelate is selected from the group consisting of selenium amino acid chelates, copper amino acid chelates, zinc amino acid chelates, manganese amino acid chelates, iodine amino acid chelates, and chromium amino acid chelates.

3. A dietary supplement for the prevention and treatment of excessive intestinal permeability, the supplement including selected amounts of calcium carbonate, sodium sesquicarbonate, magnesium oxide, dimethyl glycine HCL, one or more vitamins selected from the group consisting of vitamins A, B-complex, D and E, and one or more amino acid chelates selected from the group consisting of selenium amino acid chelates, copper amino acid chelates, zinc amino acid chelates, manganese amino acid chelates, iodine amino acid chelates and chromium amino acid chelates.

4. A dietary supplement for the prevention and treatment of excessive intestinal permeability, the supplement including selected amounts of a first carbonate component, a second carbonate component, an oxide, one or more vitamins, and one or more amino acid chelates, said second carbonate component being selected from the group consisting of sodium sesquicarbonate and the ionic equivalent of sodium sesquicarbonate.

5. The dietary supplement of claim 4, further including a selected amount of dimethyl glycine HCL.

6. The dietary supplement of claim 4, wherein said one or more vitamins is selected from the group consisting of vitamins A, B-complex, D and E.

7. The dietary supplement of claim 4, wherein said one or more amino acid chelates is selected from the group consisting of selenium amino acid chelates, copper amino acid chelates, zinc amino acid chelates, manganese amino acid chelates, iodine amino acid chelates and chromium amino acid chelates.

8. The dietary supplement of claim 4, wherein said first carbonate component is provided in an amount of approximately 60% by weight, said second carbonate component is provided in an amount of approximately 27% by weight, and said oxide is provided in an amount of approximately 5% by weight.

9. The dietary supplement of claim 4, wherein said first carbonate component is provided in an amount of over half of the total weight of the supplement and said second carbonate component is provided in an amount of about half the weight of said first carbonate component.

10. A dietary supplement for the prevention and treatment of excessive intestinal permeability, the supplement including a selected amount of a first carbonate component, a selected amount of a second carbonate component, and a selected amount of Vitamin E, said selected amount of said first carbonate component being about 60% by weight and said selected amount of said second carbonate component being about half by weight of said first carbonate component.

11. The dietary supplement of claim 10, wherein said second carbonate component is sodium sesquicarbonate.

12. The dietary supplement of claim 10, further including a selected amount of dimethyl glycine HCL.

13. The dietary supplement of claim 10, further including one or more vitamins selected from the group consisting of vitamins A, B-complex, D and E.

14. The dietary supplement of claim 10, further including one or more amino acid chelates selected from the group consisting of selenium amino acid chelates, copper amino acid chelates, zinc amino acid chelates, manganese amino acid chelates, iodine amino acid chelates and chromium amino acid chelates.

* * * * *